United States Patent [19]

Lariccia et al.

[11] 3,943,928
[45] Mar. 16, 1976

[54] ELIMINATING THE SAFETY HAZARD IN ORAL DISSOLUTION OF A SOLID

[76] Inventors: Anthony H. Lariccia, 4675 Village St., Erie, Pa. 16506; Mary L. Lariccia, 1596 W. 30 St., Erie, Pa. 16508

[22] Filed: Sept. 25, 1974

[21] Appl. No.: 509,215

[52] U.S. Cl. .................................. 128/260; 128/267
[51] Int. Cl.² .......................................... A61M 35/00
[58] Field of Search ..... 128/260, 267, 2 W; 426/72, 426/75, 104, 134; 424/18

[56]  References Cited
UNITED STATES PATENTS

| | | | |
|---|---|---|---|
| 1,586,137 | 5/1926 | Zanath | 426/104 |
| 1,668,524 | 5/1928 | Bogue | 426/104 |
| 1,936,816 | 11/1933 | Zitzman | 426/104 |
| 3,290,157 | 12/1966 | Schwartz et al. | 426/104 X |
| 3,319,621 | 5/1967 | Schwerin | 128/2 W |
| 3,506,009 | 4/1970 | Pietro | 128/267 |
| 3,508,547 | 4/1970 | Deuschle | 128/260 |

FOREIGN PATENTS OR APPLICATIONS

| | | | |
|---|---|---|---|
| 469,765 | 11/1950 | Canada | 426/75 |

OTHER PUBLICATIONS

"Medicated Candies" Q. S. Magazine Vol. No. 1 Apr., 1952 – p. 18.

*Primary Examiner*—Aldrich F. Medbery
*Attorney, Agent, or Firm*—Shanley, O'Neil and Baker

[57] ABSTRACT

Structure for safely administering a medication orally in which a soluable medicated body is maintained on a rod during dissolution by the configuration of that portion of the rod embedded in the medicated body. A method of manufacturing an enlarged end for the rod comprises forming convolutions of coiled sheet material in which the sheet material is embossed before coiling. Handle means in angled relation to the rod and spaced from the medicated body prevents inadvertent swallowing of the medication and/or the rod. The handle means can be unitary with the rod or separable and reusable being made integral by a resilient gripping means.

13 Claims, 16 Drawing Figures

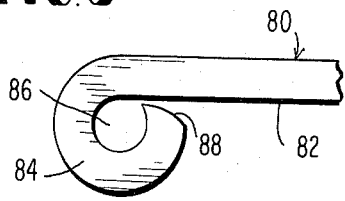
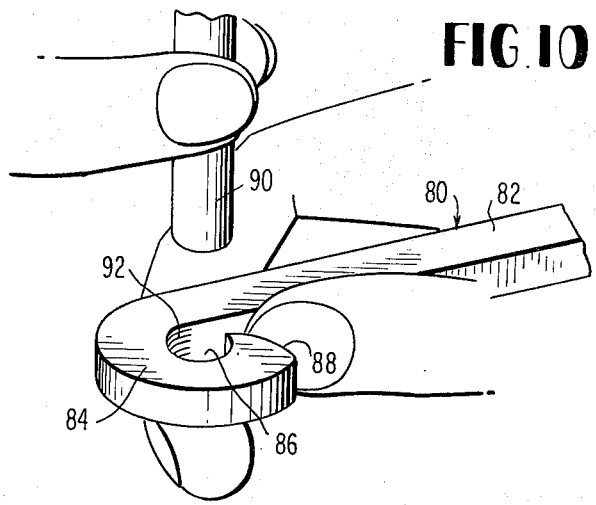
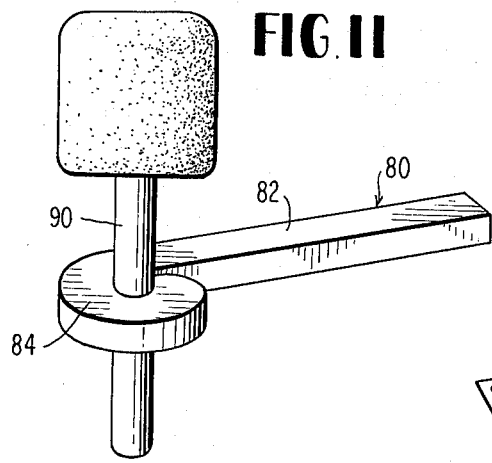
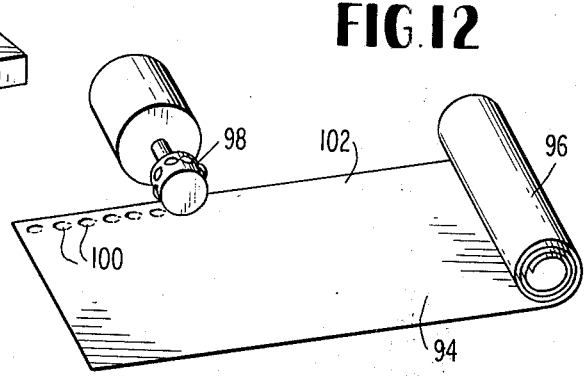
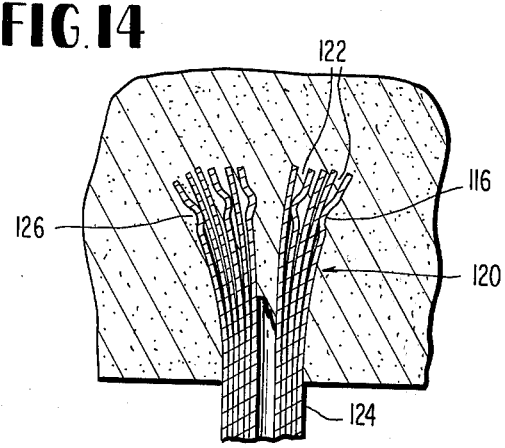
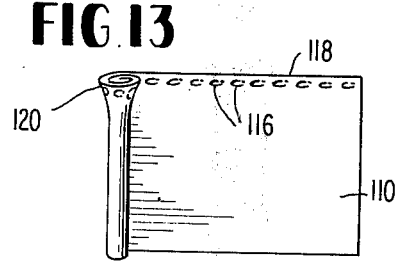
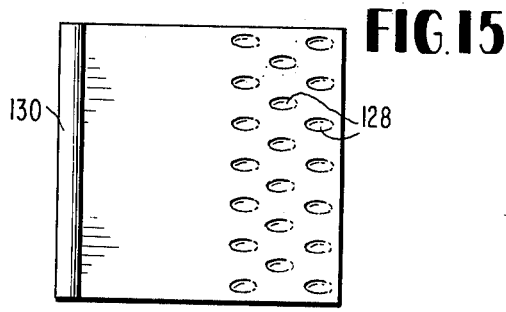
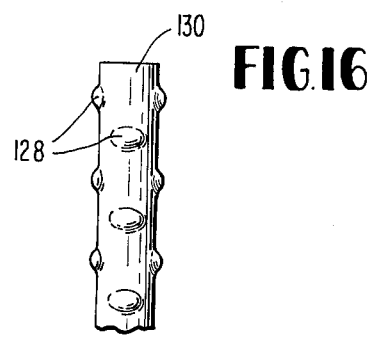

ELIMINATING THE SAFETY HAZARD IN ORAL DISSOLUTION OF A SOLID

The invention is concerned with eliminating the hazard to safety in oral dissolution of a solid. More particularly, the invention relates to means for safely administering medication orally and to methods of manufacturing of such means.

In administering medication orally and gradually, e.g. medication which would be helpful in supplying cough relief for children, ordinary lozenges or cough drops present an inherent danger of inadvertent swallowing due to their small size and with the involuntary inhaling that occurs with sneezing or coughing. The danger of accidental swallowing is increased for children or adults when such medication is applied during bed rest.

Such dangers and other shortcomings of the prior means of applying medication orally are overcome by the present invention which provides means and methods of manufacturing such means for safely administering medication orally. A continuous search of medication is made available to provide continuous relief.

Novel concepts and contributions of the invention are illustrated by the accompanying drawings. In these drawings:

FIG. 9 is a plan view of a separable safety handle means embodying the invention;

FIG. 10 is a perspective view of the safety handle means of FIG. 9 showing the manner in which the handle means is spread to receive a rod;

FIG. 11 is a perspective view of the safety handle means of FIG. 9 clamped in position for use on a rod;

FIG. 12 shows a first step in the method of preparing a web of sheet material to form an enlarged end rod in accordance with the invention;

FIG. 13 shows the step of coiling the web of FIG. 12 to form such enlarged end;

FIG. 14 shows the finished rod, partly in cross section, and the manner in which the enlarged end improves adherence and secures the rod against removal from the medication.

FIG. 15 shows coiling of sheet material to form another embodiment of the rod means of the present invention; and FIG. 16 is an enlarged, fragmentary cross-sectional view of the rod means being formed in FIG. 15.

In the accompanying drawings and the following detailed disclosure, the use described is a cough remedy type of medication. This medication can take the form of any of the well-known palliatives, demulcents, alleviants, or expectorants, antihistamines or other types of medication, often in a carrier. The medication, per se, is not part of the invention and can be prescription or non-prescription type. Such medication can comprise a hard sugar-base type, such as is used in the wellknown cough drop, or a taffy-like carrier.

An important concept of the invention is concerned with means for retention of a medication on a rod or stick during its dissolution in the oral cavity. This concept provides for retention and dissolution, continuously and gradually, reducing the opportunity for easy removal of a medication before dissolution and thus helps avoid the danger of asphyxia due to swallowing; a hazard to safety encountered with the ordinary cough drop.

Figure 1:
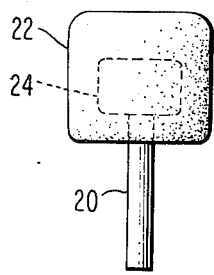
FIG. 1 is a front view in elevation with a dotted line portion representing schematically a retention feature of the invention.

As shown in FIG. 1, a portion of rod 20 is embedded in medicated body 22. The embedded portion 24, shown in dotted lines, represents means for retention of the medicated body 22 on the rod 20.

Figure 2:
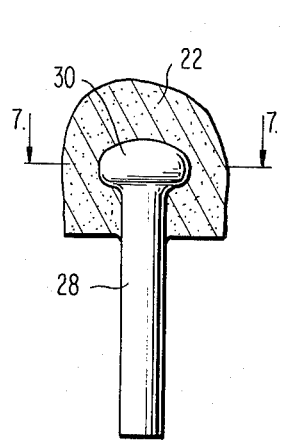
FIGS. 2 through 6 are enlarged, fragmentary, sectional views of retention means of the invention.
Figure 7:
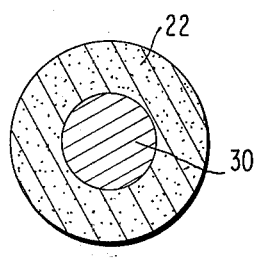
FIG. 7 is a traverse sectional view of FIG. 2 taken along the lines 7—7.

Retention means 24, schematically illustrated in FIG. 1, can take the form of varying cross-sectional configurations wherein the varying cross section contributes to the retention of medicated solid 22 on the rod. As shown in FIG. 2, a portion of the embedded rod 28 takes the form of a domeshaped head 30. Preferably, as shown in FIG. 7 which is a cross-sectional view transverse to the longitudinal axis of rod 22, the medicated body 22 should have a configuration so that the enlarged head 30 is approximately uniformly spaced from the external surface portions of the medication for purposes of uniform dissolution and substantial uniformity of the retention aspects as the medication dissolves.

Figure 3:
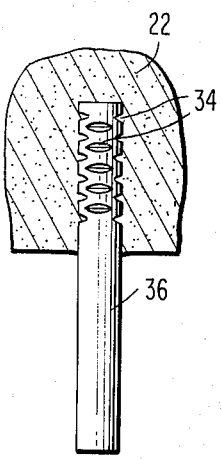
Figure 4:
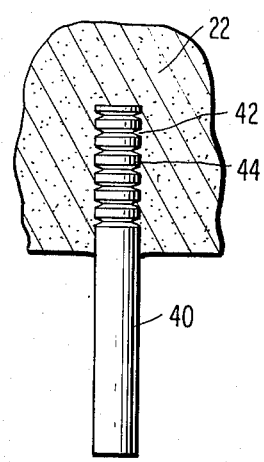
Figure 5:
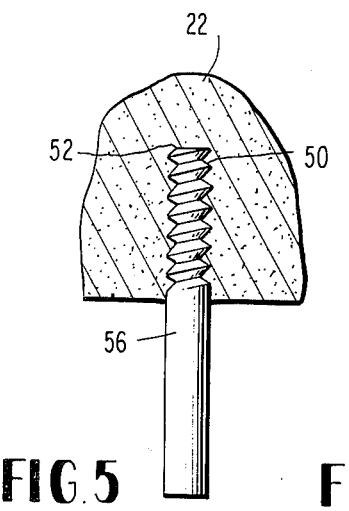

In the embodiments of FIGS. 3 through 5, a plurality of serrations, in transverse relationship to the rod means, comprise the retention means. In FIG. 3, a plurality of "V" shaped notches 34 are distributed about the periphery of rod 36. Such notched portion is embedded in the medication when the latter is in a semi-molten or plastic state so that the medication fills such preformed slots. This serrated configuration extends over at least a major portion of the embedded portion of rod 36. In accordance with the teachings of the invention, such serrations can extend over the full length of rod 36 and a unitary handle means to serve as an improved grip.

In FIG. 4 the grooves 42, which are of reduced diameter in relation to remaining portions 44, extend around the entire periphery of rod 40.

In FIG. 5, the varying cross-sectional configuration of rod 48 comprises the screw threads 50 at the embedded end 52 of rod 56. The V-shaped notches of FIG. 3, the peripheral grooves of FIG. 4, and the screw threads of FIG. 5 have a number of advantages in manufacture and application. These shapes can be readily formed in wood, plastic, or paper composition rods by cutting, molding, pressing, crimping, or embossing, or by embossing the sheet material from which the rod is formed as described later. Further, such configurations are readily insertable into medication when in the semi-molten or plastic state; the medication readily fills the recesses in the periphery to enhance the retentive strength. Further, such recesses can be readily extended over the full length of the rod.

Figure 6:
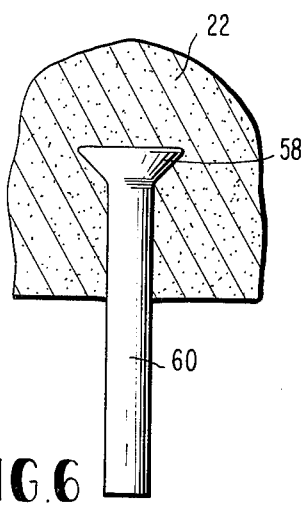

In the embodiment of FIG. 6 a tapered head 58 is formed in rod 60. The tapered portion can have the configuration of a truncated cone with, preferably, its smaller end directed toward the external handle portion of rod 60. As described in relation to FIG. 2, the external surface configuration of the medication can generally conform to this tapered shape to facilitate uniform dissolution and retention. Also internal portions of the medicated body, especially with the domeshaped head of FIG. 2 and the tapered head configuration of FIG. 6 can comprise a taffy-like confection which will facilitate molding and retention on these shapes. In such embodiment the medication can be coated on such internal portion.

A common characteristic of the safety features of FIGS. 2 through 6 is that the embedded portions of these handles are of varying cross section so as to firmly and effectively secure the rod means to the medicated solid together, decreasing the danger of inadvertent removal of the medication. Other safety features of the invention substantially eliminate swallowing by a person using a solid, soluable medication.

Important to the safety concept of the present invention is the prevention of injury during use; e.g., by falling on or bumping of the rod used for administering the medication. Further the invention provides means to prevent injury by swallowing of the medication, carrier, or administering means. Broadly this safety concept involves use of handle means in angled relationship to the medication support rod. Such handle means are predeterminedly spaced from the end of the medicated solid so as to prevent swallowing and asphyxia. The physical dimensions and spacing of the handle means prevent insertion in the mouth and also, because of the angled relation to the rod, turn the orally soluable solid and administering rod to the side in case of accidental bumping.

Figure 8:
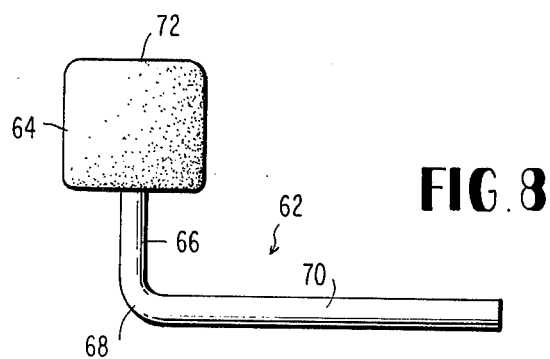
FIG. 8 is a front view embodying the invention in elevation of an embodiment of the invention having a unitary safety handle embodying the invention.

A preferred way of carrying out this novel concept in a simplified and economical way is shown in FIG. 8. A rigid or semi-rigid means, which can be firmly gripped so as to be easy to use and control, is used for administering a medication. A unitary, L-shaped structure 62 is provided for this purpose. An orally soluable solid 64 is held on rod portion 66 which is embedded in the solid 64. At juncture 68, unitary handle 70 extends in transverse relationship to the longitudinal axis of rod portion 66. A perpendicular relationship is shown and preferred, but satisfactory safe functioning can be obtained with an internal angle between rod portion 66 and handle portion 70 in the range of about 60° to about 120°.

The spacing between juncture 68 and solid body 64 is predetermined so that the distance from end 72 of body 64 to the axis of handle arm 70 at handle juncture 68 is less than the distance from the lips to the throat of a user. Generally, for children's use, this distance should be less than two inches.

The longitudinal dimension of handle arm 70 is selected so as to prevent insertion of the handle portion in the mouth. If handle arm 70 is contacted toward its longitudinal end, angled turning of the rod portion 66 and the soluable solid 64 occurs within the mouth of the user. Accidental bumping close to juncture 68 causes arm 70 to contact the face of the user before swallowing of solid 64 can occur.

Safety aspects of the invention in providing a handle means for a rod retaining an orally dissolvable solid can be extended to lollipop-type sticks, e.g. by the embodiment shown in FIGS. 9 through 11. The handle means of such embodiment is made integral with a rod or stick carrying orally soluable solid, can be positioned longitudinally as desired along such rod means, is semi-rigid rather than pliable so that it can be firmly gripped, and can be reused. This handle means is designed to be placed in angled relationship to the longitudinal axis of a rod as an obstruction to swallowing of the orally soluable solid and the rod on which it is carried.

As seen in FIG. 9, handle means 80 includes an elongated arm 82 and a working or rod gripping end 84. The latter has a curled, generally hook shaped, configuration defining aperture 86. The shape of this aperture can be selected to conform to the shape of the rod or stick with which it is made integral. That is, it can be rectilinear, or substantially circular as shown. An important dimensional aspect being that the aperture, in its normal non-expanded form, have at least one cross-sectional dimension which is less than a corresponding cross-sectional dimension of the rod or stick with which it is used.

Handle means 80 is made of material having resilient characteristics; suitable plastics for this purpose are well known. To expand aperture 86, pressure is applied to access slot edge 88. With such expansion rod 90 can be inserted as shown in Gif. 10. Rod 90 has a cross-sectional dimension permitting it to be inserted upon expansion of opening 86 and causing it to be gripped tightly by the interior sidewall of opening 86 as shown in FIG. 11 upon relief of pressure at edge 83.

Interior sidewall portions of opening 86 can be serrated with lines 92 as shown in FIG. 10. Also the opening can have sharp edge configurations to facilitate gripping. Serrations 92 can advantageously extend circumferentially and these can be further augmented by sharp edges where the aperture joins the flat upper and lower faces of the handle 80. The serrations and sharp edges can permit the handle to rotate on rod 90 but resist movement of the handle longitudinally along the rod when in the rod gripping position shown in FIG. 11. Extending the varying cross section dimensions along the rod, beyond its embedded portion, also facilitates gripping and helps prevent undesired movement of the handle means longitudinally of the rod.

The curled portion 84 of the embodiment of FIGS. 9 through 11, is of such configuration and dimension that it will not enter the mouth of a child. Also, handle arm 82 can be of sufficient length, approximately 2 to 3 inches, so as to prevent entry into the mouth either alone or in combination with the shape of the curled portion 84.

By gripping action of the material of the handle means 80, e.g. a semi-rigid plastic, it cannot be readily pulled toward or away from the orally soluable body 64. The characteristics of the handle means prevent inadvertent separation from the rod 90, yet it can be opened to enlarge the aperture 86.

A further contribution of the invention resides in an economic method of manufacturing a rod or stick with an enlarged end for retention of an orally dissolvable body or with other varying cross sectional configurations which can be extended beyond the embedded portion of the rod. With such teachings it is possible to fabricate a rod, or a plurality of rods simultaneously, from sheet material.

FIG. 12 shows schematically one step in rolling sheet material into a rod having an enlarged end. A web of sheet material 94 is fed from roll 96 through an embossing device including the embossing roller 98. Embossing roller 98 applies pressure to the sheet material forming a series of embossments or identations 100 extending along a side edge of material 102. Such embossments can be along a straight line or can be staggered. As shown in FIG. 12 the width of web 110 is approximately equal to the desired length of the rod being formed. Also this dimension can, for example, be approximately double such length and embossments formed at the opposite longitudinal end so that two enlarged end rods can be made simultaneously, and later severed. A typical sheet material would be paper of sufficient thickness and stiffness to provide a rigid, or near-rigid rod.

As shown in FIG. 13 after severing the desired longitudinal length of web 94, the web is coiled to form a stick, with the embossments 116 along its side edge 118 forming a generally wedge-shaped end 120.

As a result of the embossments, the outer surface of tapered end 120 is roughened. Also the embossments create spaces 122, as shown in FIG. 14, between the adjacent convolutions of the web which form the wedge-shaped end. These spaces fill with the semi-molten material of the orally dissolvable body applied to this end when the stick 124 is embedded in such material. As a result, an orally dissolvable body is firmly secured to the rod 124 by the material in the spaces and the roughened edges as shown at 126 in FIG. 14. Both resist separation and, the material in the spaces 122 prevents collapse of the wedge-shaped end as the material dissolves.

Suitable sheet materials which will hold embossments and provide sufficient strength in the rod are known in the art. After coiling, the edge of the final convolution can be cemented to the coiled rod body.

FIGS. 15 and 16 illustrate use of embossments 128 across the width of the web. In FIG. 15 rod 130 is being coiled with the final convolution, or last several convolutions, including embossments. The varying cross section configuration resulting from such embossments is shown in FIG. 16.

The safety features provided by the invention have been described using several selected materials and configurations for purposes of a better understanding of the basic concepts of the invention. Modifications in these configurations and changes in materials can be resorted to within the framwork of these teachings. Therefore, the scope of the invention should be determined from the appended claims.

We claim:

1. Structure for safely administering a medication orally providing for retention of the medication in the oral cavity for dissolution while preventing inadvertent swallowing prior to dissolution, comprising
    an orally soluable body comprising a medication,
    such medicated body being mounted on an elongated rod means including a longitudinal axis,
    such rod means including an end embedded in such medicated body and a longitudinally extended non-embedded portion,
    the end embedded in such medicated body including retention means for mechanically retaining such medicated body on the rod means, and
    means for preventing swallowing during use by humans of the structure comprising
    elongated handle means having a longitudinal axis in transverse relationship to the longitudinal axis of the rod means, such handle means being integral with the longitudinally extended non-embedded portion of the rod means, and being predeterminedly spaced longitudinally from the medicated body along the non-embedded portion of the rod means with the transverse relationship of the elongated handle means defining an included angle between the longitudinal axis of the rod means and the longitudinal axis of the elongated handle means, such included angle being of a value in the range of 60° to 120°,
    such elongated handle means having a length greater than the largest opening of the oral cavity to prevent inadvertent swallowing of the medicated body and the rod means.

2. The structure of claim 1 wherein the retention means of the embedded portion of the rod means includes a dimension transverse to the longitudinal axis which is substantially greater than a corresponding dimension of the longitudinally extending non-embedded portion of the rod means.

3. The structure of claim 1 wherein the handle means is separable from the rod means and comprises
    a working end formed from semi-rigid resilient material,
    such working end defining aperture means for receiving and gripping the rod means.

4. The structure of claim 3 in which the aperture means includes
    an aperture having a cross-sectional dimension which, when in non-expanded form, is smaller than a corresponding cross-sectional dimension of the rod means, and
    slot means leading to such aperture,
    the aperture and slot means being expansible to permit insertion of the rod means into the expanded aperture.

5. The structure of claim 4 in which the slot means includes
    edge means for opening the slot means and expanding the aperture, the resilient characteristics of the semi-rigid material causing the working end of the handle means to tenaciously grip the rod means after insertion in the aperture upon release of the edge means for opening the slot means.

6. The structure of claim 1 in which such elongated handle means is unitary with the rod means.

7. An oral treatment device comprising
    a saliva dissolvable cough-relief lozenge, and a means for preventing admission into the throat passageway including
    an L-shaped rod means,
    the L-shaped rod means having at least a portion of one leg embedded in such lozenge and a remaining leg projection in angled relationship to the leg having a portion embedded in the lozenge, such angled relationship defining an included angle having a value between 60° and 120°,
    such remaining angled leg being of sufficient length to prevent inadvertent swallowing during use by humans of the lozenge and rod means.

8. The combination of claim 7 wherein,
    the remaining leg extends at an angle of approximately 90° to the leg having a portion embedded in the lozenge.

9. A method of forming longitudinally extended rod means for safely retaining an orally dissoluable solid comprising the steps of
    providing a web of sheet material,
    forming a plurality of embossments on the sheet material,
    coiling such embossed sheet material to form an elongated rod, the embossments defining a varying cross-sectional configuration on the external surface of the coiled rod, and
    embedding one longitudinal end of the rod having the varying cross-sectional configuration in orally dissoluable material while such material is in a plastic state.

10. The method of claim 9 in which the embossments are formed contiguous to one edge of the sheet material in the direction of coiling forming a configuration contiguous to such embossments having a larger diameter than the remaining nonembossed coiled portion, and such enlarged cross section embossed portion of the rod is embedded in the orally dissoluable material while such material is in a plastic state.

11. The method of claim 9 in which the embossments maintain spaces between convolutions of the sheet material at one end of the rod and the embedding of the rod causes such plastic body of material to enter the spaces between the convolutions contiguous to the embossments.

12. Structure for safely administering a medication orally providing for retention of the medication in the oral cavity for dissolution while preventing inadvertent swallowing prior to dissolution, comprising an orally soluble body comprising a medication, such medicated body being mounted on an elongated rod means including a longitudinal axis, such rod means including an end embedded in such medicated body and a longitudinally extended non-embedded portion, the end embedded in such medicated body including retention means for mechanically retaining such medicated body on the rod means, such rod means being formed from a web of sheet material preformed with embossments along one edge and then coiled into an elongated rod, such embossments forming the retention means by providing a varying cross-sectional diameter configuration of substantially greater diameter than the remainder of the rod means, and elongated handle means in transverse relationship to the longitudinal axis of the rod means and located along the longitudinally extended non-embedded portion of the rod means, such handle means being of sufficient length to prevent inadvertent swallowing of the medicated body and the rod means.

13. The structure of claim 12 in which the embossments provide spaces between convolutions of the rolled sheet material, which spaces are filled by material of the orally soluable body to help prevent deformation of the varying cross section configuration and inhibit separation of the orally soluble body from the rod means.

* * * * *